United States Patent [19]

Hoftman

[11] Patent Number: 5,738,094
[45] Date of Patent: Apr. 14, 1998

[54] ANESTHESIA/RESPIRATOR MASK WITH REDUCED NASAL SECTION ENCLOSURE AND INFLATABLE CUFF

[76] Inventor: Moshe Hoftman, 22205 Dardenne Ave., Calabasas, Calif. 91302

[21] Appl. No.: 697,861

[22] Filed: Aug. 30, 1996

[51] Int. Cl.$^6$ ............................ A62B 18/08; A62B 18/02
[52] U.S. Cl. ................... 128/206.26; 128/206.24; 128/206.28
[58] Field of Search ................. 128/206.21, 206.23, 128/206.24, 206.26, 206.28

[56] References Cited

U.S. PATENT DOCUMENTS

| | | |
|---|---|---|
| D. 293,613 | 1/1988 | Wingler . |
| D. 323,908 | 2/1992 | Hollister et al. . |
| 790,057 | 5/1905 | Hively . |
| 1,206,045 | 11/1916 | Smith . |
| 1,287,149 | 12/1918 | Walter et al. ............... 128/206.24 |
| 1,632,449 | 6/1927 | McKesson ............... 128/206.24 |
| 2,313,999 | 3/1943 | Kreiselman . |
| 2,435,721 | 2/1948 | Lehman ............... 128/206.24 |
| 2,535,938 | 12/1950 | Lombard . |
| 2,625,155 | 1/1953 | Engelder . |
| 2,765,788 | 10/1956 | Raiche . |
| 2,875,757 | 3/1959 | Galleher et al. . |
| 3,042,035 | 7/1962 | Coanda . |
| 3,330,274 | 7/1967 | Bennett ............... 128/206.26 |
| 3,982,532 | 9/1976 | Halldin et al. ............... 128/206.24 |
| 4,062,357 | 12/1977 | Laerdal . |
| 4,201,205 | 5/1980 | Bartholomew . |
| 4,347,205 | 8/1982 | Stewart . |
| 4,384,577 | 5/1983 | Huber et al. ............... 128/206.24 |
| 4,559,940 | 12/1985 | McGinnis . |
| 4,803,981 | 2/1989 | Vickery . |
| 4,905,686 | 3/1990 | Adams ............... 128/206.21 |
| 4,913,401 | 4/1990 | Handke . |
| 5,121,745 | 6/1992 | Israel . |

OTHER PUBLICATIONS

"Understanding Anesthesia Equipment", JA Dorsch et al. pp. 363–392, Williams & Wilkins, 1984.
*Stedman's Medical Dictionary*, 26th ed., Marjory Spraycar, ©1995, Williams & Wikins, Baltimore, MD, 21201, USA, ISBN #0683079220.

*Primary Examiner*—Kimberly L. Asher

[57] ABSTRACT

The present invention is an inflatable cuff type anesthesia mask with three methods of improved support shell orientation of the inflatable cuff in combination with and to enable the successful operation of the mask at a point substantially more inferior on the bridge of the nose than currently shown in the prior art.

22 Claims, 4 Drawing Sheets

ANESTHESIA/RESPIRATOR MASK WITH REDUCED NASAL SECTION ENCLOSURE AND INFLATABLE CUFF

BACKGROUND OF THE INVENTION

The present invention relates to anesthesia and respirator masks typically used in the medical arts.

The section of the book by J. A. Dorsch et al, pp. 363–392 of "Understanding Anesthesia Equipment" (Williams & Wilkins, 1984) describes several popular types of anesthesia masks. An important aspect of the anesthesia mask noted on page 363 is that of the two types of face seal "One is a cushion (rim pad) that is inflated with air or filled with a material that will conform to the face when pressure is applied. The second type of seal is a flange that is an extension of the body." Masks that can be widened or narrowed to fit the face are shown in FIG. 13.1 and 13.2 are a hybrid of the above two types. The interior void which is inflated and extends from the face seal section of their double rubber shell construction up to the connector orifice. This type of mask is in contrast to those inflatable masks whose inflatable portion is separate from the dome or semi-spherical external support shell necessary to connect a flexible inflatable cuff with the connector orifice.

In the Dorsch book, the Laerdal mask of FIG. 13.8 is an example of the single support shell/inflatable cuff mask. It is further noted on page 367 that "The best fit is obtained by selecting a mask and testing it before induction of anesthesia. The smallest mask that will do the job is the most desirable because it will cause the least increase in dead space, will usually be easiest to hold, and will be less likely to result in pressure on the eyes." The very serious implications of failing to obtain a gas tight seal between the gas delivery conduits and the face of the wearer has made each of the above factors the focus of specific improvements in the art. The problems associated with masks in the art are shown and described on pages 367–368, especially directed to FIG. 13.11. In that FIG. 13.11, the Laerdal mask is shown being held in place with one hand, the most common and desirable method since the anesthesiologist or nurse will then have one hand free to use for other tasks. It will readily occur to the skilled person that there is tremendous potential for a failure to maintain a gas tight seal about the patient's mouth and nose, especially in the cheek area as the masseter/buccinator muscles form a rather softer area for which the seal must be maintained. The single support shell/inflatable cuff mask is especially prone to this failing due to the lack of sensible response of the separation of the inflated cuff from the cheek. The second type of mask described above may more readily alert the anesthesiologist or nurse of a gas seal break or leak in the cheek area because the edges of the firm face seal flange do not extend substantially outwardly beyond the effective sealing edge to obscure the flange/skin seal. However, an unsymmetrical facial bone structure or musculature of the patient or a failure to maintain a relatively narrow range of downward orientation of the non-inflatable cuff mask makes the flange type of mask more difficult to maintain in a gas tight seal than the mask with an inflatable cuff.

U.S. Pat. No. 790,057 shows an early inhaler anesthesia mask. A generally inward curvature is seen in FIG. 2 showing an adaptation for the bridge of the nose of a patient.

U.S. Pat. No. 1,206,045 shows a nasal inhaler with a hard, gas tight support shell with "flange" or plastic material to be situated between the shell and the patient as sealing means.

U.S. Pat. No. 2,313,999 generally shows a double shelled mask similar to that of FIG. 13.1 of the Dorsch book. The double shell comprises generally quite firm but flexible rubber and extends from the seal to the gas conduit at the orifice connector to the variable diameter expanded section at the face-contacting portion of the double shell. In contrast to the Laerdal mask shown in the Dorsch book downward pressure on the supports shell generally presses the "flange" face contact surface in a direction outward from the axis formed by the orifice connector. In another aspect of this outward motion of the sealing surface of the "flanges" of the non-inflatable cuff type mask, the skin of the patient is drawn away from the nose and mouth. The opposing action of reacting skin and musculature improves the pressure of and increases surface area of the sealing contact surface area between the mask and the patient.

U.S. Pat. Nos. 2,535,938, 2,625,155, 2,765,788 and 3,042,035 generally show masks with relatively hard "flange" material. So although downward pressure tends to increase the seal by causing a reaction of opposing skin and muscles, the relatively narrow "flange" material almost eliminates this advantage and, for the face with extensive wrinkling in old age, will tend to "trap" the creases in the skin between the harder "flange" material and permit gas to flow between the atmosphere into the mask or vice versa.

U.S. Pat. No. 2,875,757 describes an inflatable cuff type mask. FIG. 3 very clearly shows the cuff cross-section. FIG. 4 shows how the inflated cuff looks and presents an inward facing sealing surface. In a cross section of the mask through an axis formed through the axis of the orifice of the orifice connector, it is seen that the support shell outwardly and away from the orifice connector and over the inflatable cuff such that the bottom most extended surface of the inflated cuff extends only slightly beyond the rim of the support shell. Downward pressure on the outside of the mask to form a seal with the patient's face necessitates the inflated cuff be pressed inward. The greatest pressure that may be applied to such a mask is limited to that pressure within which the cuff will maintain a clearance between the patient's face and the hard support shell.

U.S. Pat. No. 3,982,532 shows another double shell mask construction where the void formed extends from the face contact surface to the orifice connector. With careful choice of materials and with regard to relative flexibility and curvature "memory", certain embodiments of the device in this patent may, upon downward pressure of the mask to the face of a patient, may move outwardly from the nose and mouth the skin and facial muscles.

U.S. Pat. No. 4,062,357 generally shows the Laerdal mask described above. It will be seen from FIGS. 3, 6, 7 and 8 that downward pressure application to the face of a patient will cause the inflated cuff to assume a generally elliptical cross-section whereby increasing downward pressure causes the ends of the ellipse to move roughly both inward, toward the axis of the general angle of the downward pressure, and outward, away from that axis and away from the patient's nose and mouth. The result of the relatively equal inward and outward force distribution on the inflated cuff is that almost only about half of the downward pressure is transmitted to an outward motion of the cuff to facilitate a reaction of the skin and muscle back toward the nose and mouth. This is an inherent disability since the skin and musculature extending from the contact surface of the inflated cuff to the nose and mouth of the patient are generally less reactive and somewhat more elastic in that direction than in the other direction.

U.S. Pat. No. 4,201,205 shows an oxygen mask with a single firm-flexible clear plastic shell with a "flange" for improving the seal between the wearer's face and the mask. This simple construction is consistent with the limited seal needed.

U.S. Pat. No. 4,347,205 shows an inflated cuff filled with a dual lumen.

U.S. Pat. No. 4,559,940 shows an inflatable chamber for occluding a patient's mouth during airway intubation.

U.S. Pat. No. 4,803,981 shows a nose inhaler comprising only a rather firm rubber foam material. Downward pressure would tend to, as with similar "flange" type masks, move skin and muscles away from the nose.

U.S. Pat. No. 4,913,401 discloses a valve assembly generally representative of inflating valves for inflatable cuffs.

U.S. Pat. No. 5,121,745 shows a collapsible inflatable cuff mask with equal-force distribution similar to that of the above Laerdal mask.

U.S. Design Pat. No. D293,613 show an inflatable cuff type mask with inflating valve located at the nose bridge area.

U.S. Design Pat. No. D323,908 show an inflatable cuff type mask with an extension of the support shell to be, in operation, located just superior to the bridge of the nose, and providing the middle finger of the anesthesiologist or nurse with improved support.

There is a need to provide an inflatable cuff type mask wherein the benefits of the "flange" type mask may be obtained while also obtaining the increased surface contact area provided by the inflatable cuff type masks.

SUMMARY OF THE INVENTION

The present invention is an inflatable cuff type anesthesia mask with two primary methods of improved support shell orientation of the inflatable cuff in combination with and to enable the successful operation of the mask at a point substantially more inferior on the bridge of the nose than currently shown in the prior art. These improved orientations may be used separately or, more preferably, together. The first of the improved orientations is an outward chamfering of the outer edge of the support shell to such that the subsequent attachment of an inflatable cuff to the support shell and placement of the mask on the face of a patient necessarily forces substantially the greatest portion of the cross-section of the inflated cuff away from the nose and mouth of the patient. As shown in the Figures and described below, the angle of the cuff attachment means of the support shell is roughly preferably about 5–45 degrees elevated from the sealingly effective surface of the face where the inflated cuff will be depressed to form a gas tight seal. This outward chamfering is at least applied about the arch formed by the nose down to about the first contact with the face above the zygomatic bone. The chamfered extension of the support shell is most preferably applied about the entire peripheral outer edge of the support shell, obtaining the dual benefit of improved gas tight sealing from counter reaction from outwardly pushed skin and having only a single support shell to simplify manufacturing and reduce costs. More than one shell may be used in connection with the present invention, i.e., some masks have obtained various gas mixing and introduction results with more than one shell between the face and the atmosphere. However, only one support shell is needed to effect the objects of the present invention.

The second outward chamfering effect of the inflatable cuff of the present invention is to form the cuff such that downward pressure on the mask to the face of the patient causes substantially all of the deformation of the cross-section of the cuff beyond the outer rim of attachment means to the support shell. Although this special formation of the cuff is advantageous when used alone, it is more advantageous when used with the outward chamfering of the outer edge of the support shell. It is highly beneficial when both chamfering orientations are applied about the entire outer edge of the support shell of the mask whereby the medial anterior length of the facial surface covered by the mask is significantly reduced by moving the contacting/sealing surface of the inflatable cuff from a more superior to a more inferior position on the bridge of the nose. The result of reducing that medial mask length reduces the total mask contact area, thus reduces the dead space in the mask by 10–20% or more over a prior art mask with a relatively longer facial medial length.

In addition, the parison of the inflatable cuff is blow-molded, roto-molded or vinyl dipped to effect a gluing section on a substantially thicker upper or superior surface of the inflatable cuff while the remaining cuff surface comprises a relatively thin and pliable (and optionally and preferably "tacky" or slightly sticky) expandable material. This results in a far more rugged construction so that the additional stresses on the cuff of pressing the skin of the wearer outward may be made without concern for rupturing the cuff.

Thus, the outward chamfered inflatable cuff creates an opportunity to effectively and more efficiently maintain a gas tight seal over a higher arch of the nose than taught by the prior art. The mask to face sealing surface is thus withdrawn to a sufficient distance from the infraorbital arch such that even quite heavy application pressure will not result in corneal abrasion or pressure on the eye. It is within the art to provide a pre-inflated cuff or to provide a valve through which air or gas can be injected, preferably with a syringe. It is another embodiment of the present invention to provide the inflatable cuff with a dual valve whereby application of pressure between the thumb and forefinger will cause inflation of the cuff to a desired pressure, an especially advantageous feature since sustained pressure of the mask on the patient may potentially tend to cause deflation of the cuff.

In a further embodiment of the present invention, it has been found that, in contrast to any prior art mask, whether single or double shelled, a most preferred embodiment of the the chin and cheek portions of the cuff and/or outer edge of the support shell are adapted to be outwardly chamfered while the nasal bridge section, from the bridge of the nose to the maxilla, is adapted such that the effective application angle of the cuff and/or outer edge of the support shell compared to the sealing surface portion of the face is parallel or just slightly inwardly chamfered. For relatively firm application of the mask or where the cuff would tend to press above the infraorbital arch and thus into the eyelid, the parallel or slightly inwardly chamfered support shell or cuff permits adaptation to the widest range of facial curvature in the three named regions, i.e. nasal bridge, cheek (referred to later as the transition section) and chin referred to later as the mandible section).

DETAILED DESCRIPTION OF THE INVENTION

The technology disclosed below improves the art of inflatable cuffs for respirator or anesthesia masks.

The present invention will be discussed with reference to the above Figures. In the Figures, many aspects of the present invention are referred to with the same aspect item numbers in the several Figures. The use of identical item numbers indicates that the aspect identified in one Figure has substantially the features of the same aspect in another Figure. The use of several views with substantially the same aspects has been necessary to better describe the present invention.

Figure 1:
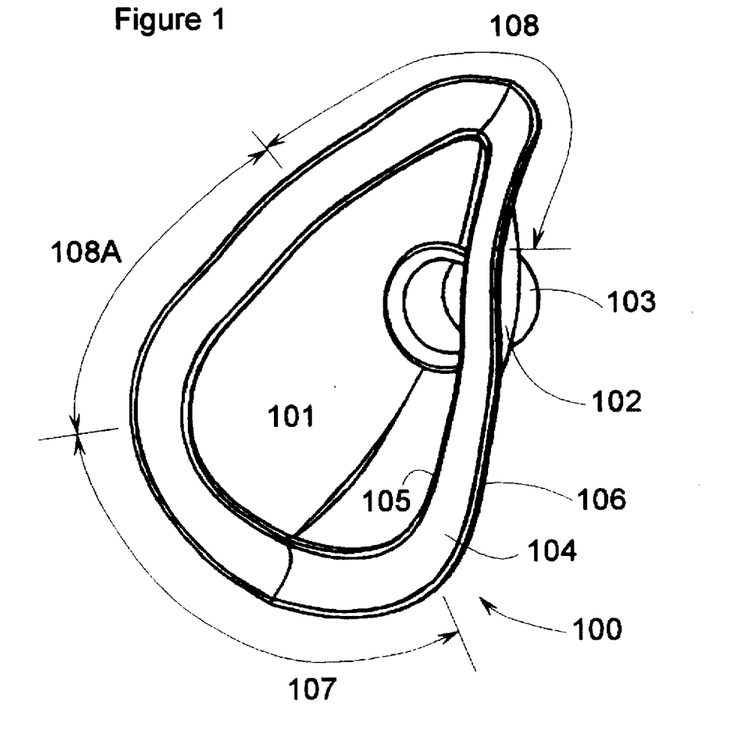
FIG. 1 is a rear view of the mask of the present invention without the inflatable cuff. The rear view is angled sufficiently to the right of rear so that the view is roughly parallel to the right side of the support shell when viewed from the rear.

FIG. 1 shows the mask of the present invention without the inflatable cuff. This is true for all the Figures except for FIGS. 8, 9, 9A and 10 so that the novel orientation and dimensions of the mask of the present invention might be clearly shown. FIG. 1 shows a mask 100 with a support shell with inside surface 101 and outside surface 102. Hose connector 103 is molded integrally with or glued or later applied to the connector orifice at the base of hose connector 103. Cuff attachment means 104 extend from the outer edge of the support shell with an inner edge 105 and an outer edge 106.

Operationally defined sections are shown in FIG. 1 to indicate sections of cuff attachment means 104 whose chamfering of the cuff attachment means 104 and cross-sectional shaping of the inflatable cuff in that section may be independent of the other sections to obtain a beneficial result for widely different facial types or desired gas seal pressures. Mandible section 107 preferably is adapted to be oriented at the lower section of or just below the inferior portion of the orbicularis oris muscle below the mouth, although it may also be adapted to be located as low as the chin of the patient. Nasal bridge section 108 preferably is adapted to be oriented at its topmost edge above the highest medial facial prominence or the most inferior external extension of the nasal bone, thereafter extending the mask down the sides of the nose bridge to the maxilla in the most direct fashion such that the length of the mask contacting surface on the nose is minimized. Transition section 108A defines the sealing section of the mask generally from the edge of the maxilla in an inferior or downward direction away from the nose but below the zygomatic bone so that the mask preferably need not be formed to seal the very difficult zygomatic to maxilla transition below the infraorbital arch. This transition section in prior art masks has not been adapted to the facial contours of the patient. The attachment ridge of the support shells in the prior art all define a relatively straight line in side view from the mandible section to the nasal bridge section. In the prior art, there has been no substantial outward flaring of the support shell in the transition or cheek section to reduce downward pressure necessary to "fill in" the cheek with the inflatable cuff, as seen in FIGS. 3, 6, and 8 of U.S. Pat. No. 4,062,357 and U.S. Design Pat. Nos. D293,613 and D323,908.

An inflatable cuff disposed along the operationally defined sections 107, 108 and 108A will thus advantageously "fill in" or more fully occupy the region between the medially directed ending of the infraorbital arch and the prominating maxilla and nasal bones. There will be no need at the most extreme pressure of the anesthesiologist or nurse at the highest downward pressure on the mask to press the upper edge of the mask over the infraorbital arch into the eye socket. An increasing downward mask pressure on the mask of the present invention will be translated into a force to move outwardly the inflated cuff in sections 108 and 108A and tend to even more effectively press the eyelids together to improve eye protection during anesthesia. The medial length of mask 100 from the midpoint of section 107 to the midpoint of section 108 is referred to herein as the nose bridge to lower orbicularis oris muscle distance and defines an effective mask length not previously used in the art. The reduction of this distance reduces the total facial surface area enclosed by mask 100 and thus also reduces dead or void space between the inside surface 101 and the face of the patient, reducing the dilution effect of gas transfer from the connecting hoses to the airway to the lungs of the patient.

Figure 2:
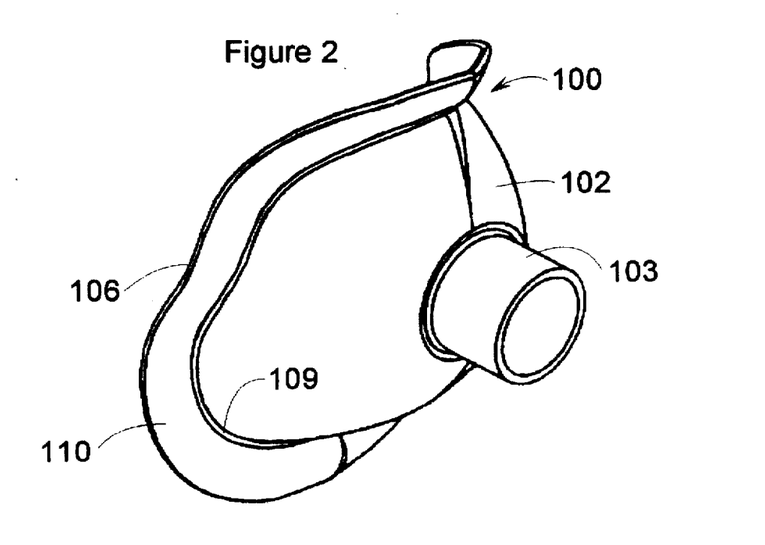
FIG. 2 is a front view of the mask of the present invention without the inflatable cuff. This front view is angled sufficiently to the left of front so that the view is roughly parallel to the right side of the support shell when viewed from the front.

FIG. 2 shows many of the features of FIG. 1, however the cuff attachment means upper surface 110 and cuff attachment means—support shell connection 109 are shown. The connection between the support shell and the cuff attachment means may be formed by integrally molding or later gluing or other effective connection that will support heavy downward pressure as is typical for application of anesthesia masks. It is this connection that in part defines an outwardly chamfering angle for the cuff attachment means 104 in the various operationally defined sections. The parabolic, roughly circular or roughly flat cross-sectional shapes that may be effectively used for the cuff attachment means also contribute to the outward chamfering of the cuff attachment means.

Figure 3:
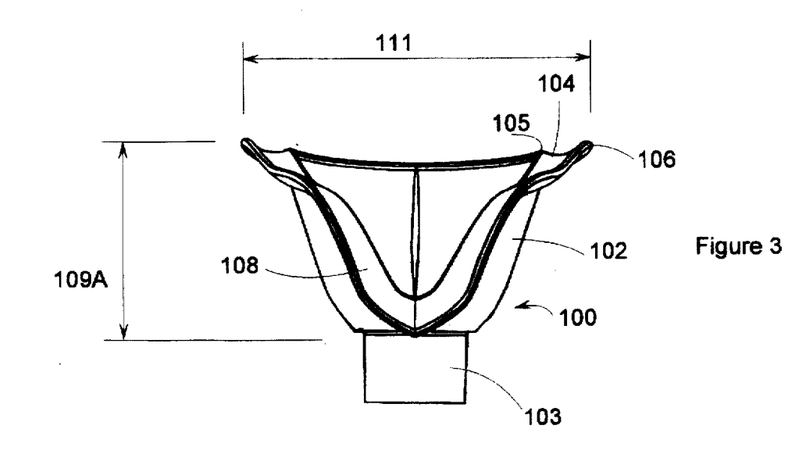
FIG. 3 is a top view of the mask of the present invention without the inflatable cuff.

FIG. 3 shows the mask of the present invention from above so that width 111 and effective height 109A can be seen. Minimizing these dimensions reduces dead space in the mask 100, although the wide variety of facial dimensions and curvatures require that several models be available to the user. Nasal bridge section 108 in FIG. 3 is seen prominently outwardly chamfered, although the degree of chamfering, as described later, is in part operationally defined so that adaptation to the facial curvature of different persons will effect a desired and preferable angle between the translated force direction of downward application pressure and the facial surface to which the inflatable cuff is applied.

Figure 4:
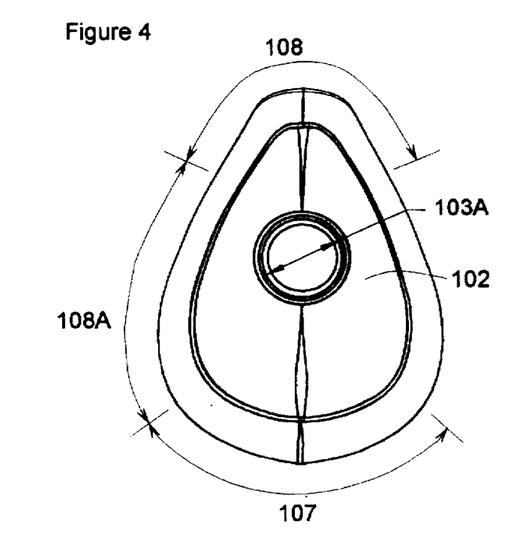
FIG. 4 is a front view of the mask of the present invention without the inflatable cuff.
Figure 5:
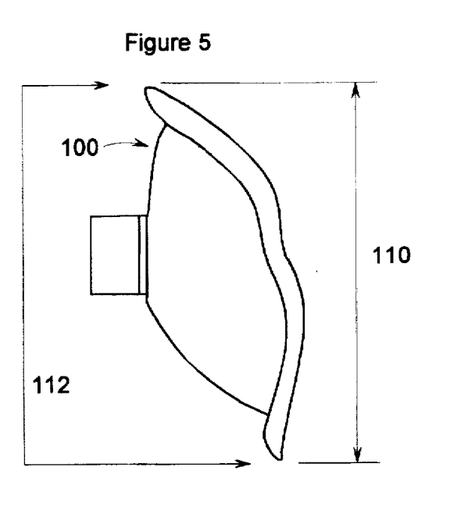
FIG. 5 is a side view of the mask of the present invention without the inflatable cuff.
Figure 6:
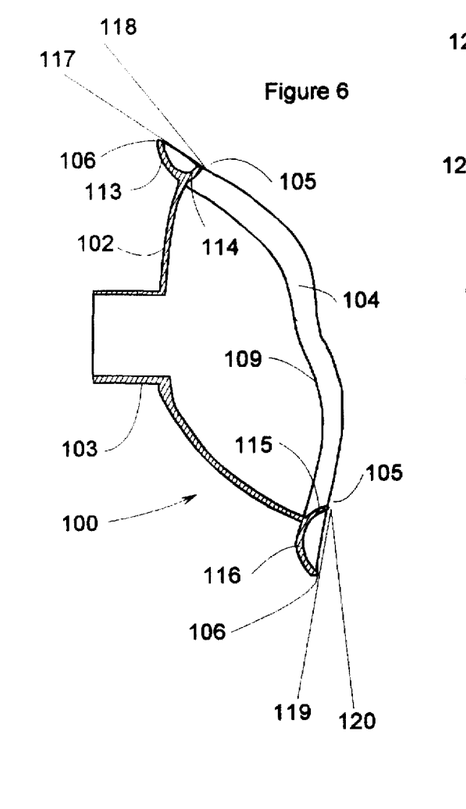
FIGS. 6, 7 and 7A are cutaway side views of the mask of the present invention without the inflatable cuff.
Figures 7, 7A:
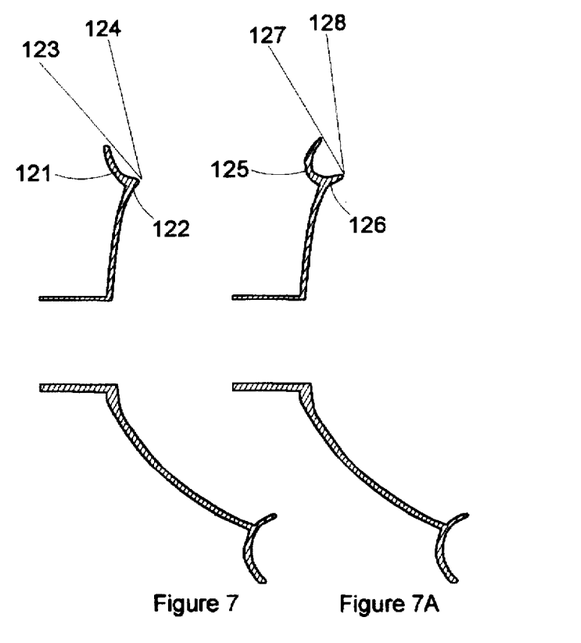

FIG. 4 shows the mask of the present invention in a front view with the diameter of the hose connector 103A defined. FIG. 5 shows a side view of the mask of the present invention with a height 110 defined by the extreme outer edges of the cuff attachment means. Medial section line 112 defines the cross-section of mask 100 for the rest of the Figures and also indicates the direction of force typically applied by medical personnel to obtain a sealing contact between the face of a patient and the mask. This force application can be seen in FIG. 13.11 of the Dorsch book. However, because operational definitions are so important to obtaining the objects of the present invention, it is known and easily observable that the direction of force applied by medical personnel on such masks is widely variable with different pressures and downward (toward the face of the patient) directions being obtainable. It is the intention of the present invention to provide chamfering that is generally effectively at an angle upwardly outward and non-parallel to the facial sealing surface of the patient, although, for this embodiment wherein the outward chamfering is supplied in the nasal bridge section, it is only critical that the nasal bridge section 108 need be provided with such chamfering. Additional benefits of the present invention are described herein for providing chamfering of the cuff attachment means in sections 107 and 108A. FIG. 6 shows a medial cross section of the mask of the present invention, showing cuff attachment means 104 such that its medial cross-sectional shapes in sections 108 and 107 are also shown, although sections 108 and 107 are not shown in their entirety as in FIG. 6. Cross-sectional shapes for sections 107 and 108 have outer cuff retaining extensions 113 and 116 respectively and inner cuff retaining extensions 114 and 115 respectively. The extreme ends of the inner and outer cuff retaining extensions generally define upward and outward chamfering directions 117 and 119. Downward pressure typically applied to the outer surface 102 by medical personnel will cause that force to be translated into a downward and outward force generally normal to the directions 117 and 119, which directions are non-parallel to facial surface directions 118 and 120 respectively. The acute angles formed by the intersection of the facial surface directions and the upward and outward directions is preferably about from 4–45 degrees, and more preferably from about 5–15 degrees. This force translation moves the attached cuff in an outward direction with respect to the nose and mouth. Another advantage of such movement is that the patient with severe wrinkling or fascia weakening such as occurs following a burn recovery will be gently spread outwardly and the wrinkles will not be trapped beneath the equal pressure cuff of the Laerdal mask. FIGS. 7 and 7A show alternate configurations of the nasal bridge section cuff attachment means. In FIG. 7, a generally minimal directioning cuff attachment means is shown with a short inner cuff retaining extension 122 and outer cuff retaining extension 121 defining direction 123 against facial surface direction 124. In FIG. 7A, a highly directioning cuff attachment means is shown with a long inner cuff retaining extension 126 and outer cuff retaining extension 125 defining chamfering direction 127 against facial surface direction 128.

Figure 7B:
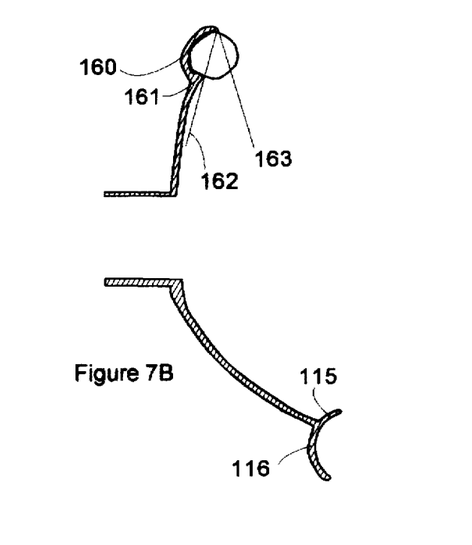
FIG. 7B is a cutaway side view of the of the mask of the present invention with an inflated inflatable cuff shown for the nasal bridge section alone.

In contrast to the nasal bridge sections of the above specific embodiments, FIG. 7B shows a nasal bridge section cross-section wherein the effective application or sealing surface of the inflatable cuff is parallel or slightly inwardly chamfered comparison to the sealing surface of the face, while the transition section and the mandible sections are outwardly chamfered as described in the embodiments above. In FIG. 7B, a generally minimal directioning cuff attachment means is shown with a short inner cuff retaining extension 161 and outer cuff retaining extension 160 defining direction 162 against facial surface direction 163. The angle formed by directions 162 and 163 are preferably from about 0 to 15 degrees to permit quite heavy pressure on the nasal bridge section while preventing abrading or impressing contact of the support shell with the surface of the patient's skin. In this embodiment, adapting the cuff attachment means and/or the cuff to provide effective outward chamfering of the cuff in the transition and mandible sections combine the advantage of low application pressure in those sections to effect a gas tight seal with the option of providing high application pressure to the nasal bridge section where it is expected that greater variation in elevation and breadth of the nose will sometimes require greater application pressure.

Figure 8:
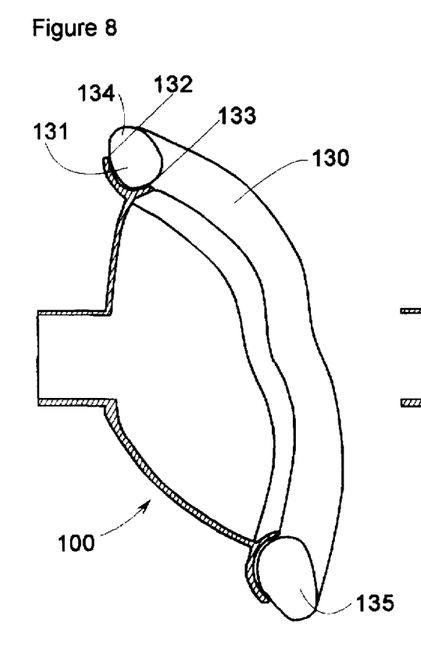
FIGS. 8, 9 and 9A are cutaway side views of the of the mask of the present invention with an inflated inflatable cuff.
Figures 9, 9A:
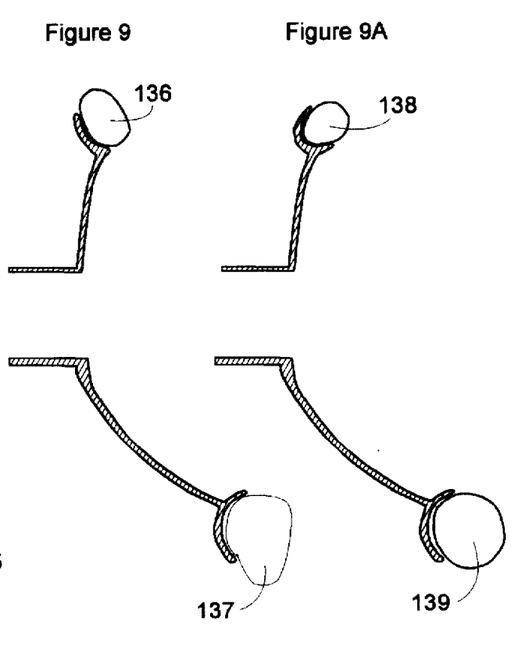

FIGS. 8, 9 and 9A show application of the several inflatable cuff cross-sectional shapes effective for obtaining the advantages of the present invention as applied to the embodiments shown in FIGS. 6, 7 and 7A. The inflatable cuff shapes 131, 135, 136, 137, 138 and 139 in the Figures indicate the many forms from circular to oblong that will be effective, however, generally the most effective shapes will have little or no inwardly lateral extension of the shape beyond the limit 133 while extending as much as 50% or more of the cross-sectional area in an outwardly lateral position past limit 132.

Figure 10:
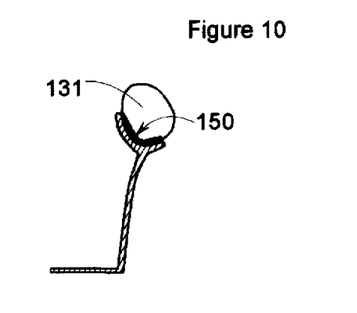
FIG. 10 is a cutaway side view of only the top half of the mask of the present invention for the purpose of showing thickness enhanced inflatable cuff with an improved surface for attachment of the inflatable cuff to the support shell.

FIG. 10 shows the thicker section 150 of inflatable cuff shape 131. Thicker section 150 is formed when blow molding the inflatable cuff on a superior surface and thereby forming a strong gluing surface. In another embodiment of the present invention, a valve and inlet tube a provided through upper surface 102 to the interior of the inflatable cuff.

The inlet tube is provided with a dual valve arrangement whereby a connector tube between the valve may be pressed with the human hand and thereby expelling air into the cuff through the proximal valve and having the distal valve seal against connector tube pressure.

It is yet another embodiment of the present invention to supply upward extensions of the upper surface 102, such as the one shown in FIGS. 2, 3, 5 and 6 of U.S. Design Pat. D323,908 (which disclosure is incorporated herein) adapted for the digits of hand of the medical personnel applying the mask of the present invention. Specifically, two extensions of the upper surface 102 are preferably adapted to be located just above the nose and mouth of a patient, such as in the location of the thumb and forefinger of the medical personnel shown in FIG. 13.11 of the Dorsch book. These are referred to herein as finger grips, permitting relatively independant pressures of application to the nasal bridge and mandible sections. Another embodiment of the present invention uses a soft, pliable synthetic foam to fill the inflatable cuff.

The support shell of the present invention may be very stiff, semi-rigid or firm and may be formed from transparent or opaque materials, although transparent, semi-rigid polymer is preferred such that the medical personnel responsible for monitoring the patient may easily view the seal formed by the chamfering of either the cuff attachment means or the inflatable cuff. In addition, it is preferred in some situations to provide the support shell with strap means whereby adjustable straps may be joined to the support shell upper surface and drawn to the back of the head and/or neck of the patient. FIG. 9 of U.S. Pat. No. 4,062,357 shows generally such plurality of upper surface extensions adapted to retain adjustable straps.

It is a further embodiment of the present invention to provide the adjustable straps with an end section for releasable and adjustable attachment to the support shell comprising a "bead and string" arrangement. The "bead and string" arrangement comprises a length preferably from about 2–12 inches whereby a polymer or equivalent material is formed with short, narrow diameter "string" sections between shorter, larger diameter "bead" sections. The support shell strap attachment comprises an extension in which is formed a hole larger in diameter than the "bead", through which the "bead and string" length may be easily passed. Another hole in the support shell strap attachment is formed laterally and in communication with the first "bead" hole, although the diameter of this second hole and the first hole lateral communication therewith are between that of the "bead" and the "string" sections. Thereby a low cost and easily latchable and unlatchable means are provided for securing the mask of the present invention without constant pressure of human hands.

The design options of the present invention will sometimes present the designer with considerable and wide ranges from which to choose appropriate modifications for the above embodiments. However, the objects of the present invention will still be obtained by the skilled person applying such design options in an appropriate manner.

I claim:

1. A respirator or anesthesia mask comprising:
   (a) a support shell with a generally dome shape;
   (b) an inflatable cuff;
   (c) cuff attachment means arranged at an outer edge of the support shell adapted to sealingly attach the inflatable cuff to the support shell and with a reduced nose bridge to lower orbicularis oris muscle distance whereby placement of the mask on a face of a person effectively situates a top edge of the cuff attachment means above a highest medial facial prominence or a most inferior external extension of the person's nasal bone and situates a bottom edge of the cuff attachment means above a lower portion of the orbicularis oris muscle;
   (d) a top edge of a cuff extension means and the attached cuff are adapted to extend down the sides of the nose bridge to the maxilla in the most direct manner, thereby defining a nasal bridge section;
   (e) the cuff attachment means of a nasal bridge section are adapted to be chamfered upwardly in relation to a facial surface contacted by the inflatable cuff in the nasal bridge section and outwardly in relation to the edge of the support shell;
   (f) the cuff attachment means are chamfered upwardly and outwardly in a mandible section; and
   (e) a chamfering of the cuff attachment means in the nasal bridge section is adapted to form a chamfering angle between the facial surface contacted by the inflatable cuff in the nasal bridge section with a chamfering direction of the cuff extension means in the range of from about 5–45 degrees.

2. The mask of claim 1 wherein the chamfering angle is in the range of from about 5–15 degrees.

3. The mask of claim 1 wherein the cuff attachment means are upwardly and outwardly chamfered about the entire periphery of the support shell.

4. The mask of claim 3 wherein the cuff attachment means further comprise an outer cuff retaining extension extending outwardly in relation to the support shell from a support shell/cuff attachment means connection and an inner cuff retaining extension extending generally in an opposing direction to the outer cuff retaining extension.

5. The mask of claim 4 wherein a cross-sectional shape formed by the cuff attachment means is formed such that the ends of the outer and inner cuff retaining means define the chamfering direction.

6. The mask of claim 5 wherein the cross-section shape of the inflatable cuff is roughly circular.

7. The mask of claim 5 wherein the cross-section shape of the inflatable cuff is roughly oblong.

8. The mask of claim 7 wherein the outer cuff retaining extension is substantially longer than the inner cuff retaining extension and a superior surface of the inflatable cuff is sealiingly distributed along the surface formed by the inner and outer cuff retaining extensions.

9. A respirator or anesthesia mask comprising:
   (a) a support shell with a generally dome shape;
   (b) an inflatable cuff;
   (c) cuff attachment means arranged at the outer edge of the support shell adapted to sealingly attach the inflatable cuff to the support shell wherein the cuff attachment means of a nasal bridge section are adapted to be chamfered upwardly in relation to a facial surface contacted by the inflatable cuff and outwardly in relation to the edge of the support shell;
   (d) the cuff attachment means are chamfered upwardly and outwardly in only a nasal bridge section; and
   (e) the chamfering of the cuff attachment means in the nasal bridge section is adapted to form a chamfering angle between the facial surface contacted by the inflatable cuff in the nasal bridge section with a chamfering direction of the cuff extension means in the range of from about 5–45 degrees.

10. The mask of claim 9 wherein the chamfering angle is in the range of from about 5–15 degrees.

11. The mask of claim 9 wherein the cuff attachment means are upwardly and outwardly chamfered about the entire outer edge of the support shell.

12. The mask of claim 11 wherein the cuff attachment means further comprise an outer cuff retaining extension extending outwardly in relation to the support shell from a support shell/cuff attachment means connection and an inner cuff retaining extension extending generally in an opposing direction to the outer cuff retaining extension.

13. The mask of claim 12 wherein a cross-sectional shape formed by the cuff attachment means is formed such that the ends of the outer and inner cuff retaining means define the chamfering direction.

14. The mask of claim 13 wherein the cross-section shape of the inflatable cuff is roughly circular.

15. The mask of claim 13 wherein the cross-section shape of the inflatable cuff is roughly oblong.

16. The mask of claim 15 wherein the outer cuff retaining extension is substantially longer than the inner cuff retaining extension and a superior surface of the inflatable cuff is sealiingly distributed along the surface formed by the inner and outer cuff retaining extensions.

17. The mask of claim 15 wherein the inflatable cuff superior surface further comprises a thickened section substantially thicker than the rest of the inflatable cuff.

18. The mask of claim 15 wherein the support shell comprises clear plastic adapted to permit viewing of a patient's skin enclosed by the mask.

19. A method for obtaining reduced dead space in a respirator or anesthesia mask comprising:
   (a) a support shell with a generally dome shape;
   (b) an inflatable cuff;
   (c) cuff attachment means arranged at the outer edge of the support shell adapted to sealingly attach the inflatable cuff to the support shell and with a reduced nose bridge to lower orbicularis oris muscle distance whereby placement of the mask on a face of a person effectively situates a top edge of the cuff attachment means above a highest medial facial prominence or a most inferior external extension of the person's nasal bone and situates a bottom edge of the cuff attachment means above a lower portion of the orbicularis muscle; and (d) applying the mask to face of a patient with pressure typical for obtaining a gas tight seal around the nose and mouth of the patient;

(e) the top edge of the cuff extension means and the attached cuff are adapted to extend down the sides of the nose bridge to the maxilla in the most direct manner, thereby defining a nasal bridge section;

(f) the cuff attachment means of the nasal bridge section are adapted to be chamfered upwardly in relation to a facial surface contacted by the inflatable cuff in the nasal bridge section and outwardly in relation to the edge of the support shell;

(g) the cuff attachment means are chamfered upwardly and outwardly in a mandible section; and (h) the chamfering of the cuff attachment means in the nasal bridge section is adapted to form a chamfering angle between the facial surface contacted by the inflatable cuff in the nasal bridge section with a chamfering direction of the cuff extension means in the range of from about 5–45 degrees.

20. The method of claim 19 wherein the chamfering angle is in the range of from about 5–15 degrees.

21. The method of claim 19 wherein the cuff attachment means are upwardly and outwardly chamfered about the entire periphery of the support shell.

22. A respirator or anesthesia mask comprising:

(a) a support shell with a generally dome shape;

(b) an inflatable cuff;

(c) cuff attachment means arranged at the outer edge of the support shell adapted to sealingly attach the inflatable cuff to the support shell wherein the cuff attachment means of a nasal bridge section are adapted to be parallel or chamfered slightly upward in relation to a facial surface contacted by the inflatable cuff and inward in relation to the edge of the support shell;

(d) the cuff attachment means of the rest of the mask adapted to be chamfered upwardly in relation to a facial surface contacted by the inflatable cuff and outwardly in relation to the edge of the support shell; and (e) the chamfering of the cuff attachment means in the nasal bridge section is adapted to form a chamfering angle between the facial surface contacted by the inflatable cuff in the nasal bridge section with a chamfering direction of the cuff extension means in the range of from about 0–15 degrees.

* * * * *